US010376623B1

(12) United States Patent
Tawakol

(10) Patent No.: US 10,376,623 B1
(45) Date of Patent: Aug. 13, 2019

(54) SUBCLAVIAN DIASTOLIC AUGMENTATION DEVICE

(71) Applicant: Raif Tawakol, Glendale, AZ (US)

(72) Inventor: Raif Tawakol, Glendale, AZ (US)

(73) Assignee: Raif Tawakol, Stoughton, MA (US)

( * ) Notice: Subject to any disclaimer, the term of this patent is extended or adjusted under 35 U.S.C. 154(b) by 0 days.

(21) Appl. No.: 15/946,702

(22) Filed: Apr. 5, 2018

(51) Int. Cl.
*A61M 1/12* (2006.01)
*A61M 1/10* (2006.01)
*A61L 31/02* (2006.01)
*A61L 31/04* (2006.01)
*A61F 2/06* (2013.01)

(52) U.S. Cl.
CPC .......... *A61M 1/122* (2014.02); *A61L 31/022* (2013.01); *A61L 31/024* (2013.01); *A61L 31/042* (2013.01); *A61M 1/1008* (2014.02); *A61M 1/1086* (2013.01); *A61F 2/06* (2013.01); *A61M 2205/3523* (2013.01); *A61M 2205/8206* (2013.01); *A61M 2230/30* (2013.01)

(58) Field of Classification Search
None
See application file for complete search history.

(56) References Cited

U.S. PATENT DOCUMENTS

| | | | | |
|---|---|---|---|---|
| 3,911,898 | A | * 10/1975 | Leachman, Jr. | A61M 1/122 600/17 |
| 4,381,567 | A | * 5/1983 | Robinson | A61M 1/1044 417/383 |
| 2007/0100196 | A1 | * 5/2007 | LaRose | A61M 1/101 600/16 |
| 2017/0224894 | A1 | * 8/2017 | Najar | A61M 1/122 |
| 2017/0258981 | A1 | * 9/2017 | Franano | A61M 1/3653 |

OTHER PUBLICATIONS

Schreuder et al., "Automatic Intraaortic Ballon Pump Timing Using an Intrabeat Dicrotic Notch Prediction Algorithm", 2005, https://www.sciencedirect.com/science/article/pii/S0003497504016418?via%3Dihub, Nov. 1, 2018.*

* cited by examiner

Primary Examiner — Christopher Koharski
Assistant Examiner — James Moss
(74) Attorney, Agent, or Firm — Malone IP Law; Steven J. Malone

(57) ABSTRACT

A minimally invasive pre-cardiogenic heart assist device has been developed. A method of increasing myocardial blood flow using a Subclavian Diastolic Augmentation Device (SDAD) includes grafting a subclavian vein to a first synthetic chamber, the first synthetic chamber located inside of a body of the patient; grafting a subclavian artery to a second synthetic chamber, the second synthetic chamber located inside of the body of the patient; and pumping blood from the first synthetic chamber to the second synthetic chamber with a pump located inside of the body of the patient.

17 Claims, 10 Drawing Sheets

SUBCLAVIAN DIASTOLIC AUGMENTATION DEVICE

FIELD OF THE INVENTION

The present invention discloses a device and method for increasing myocardial blood flow in a patient during pre-cardiogenic shock, hemodynamic instability due to myocardial infarction, high-risk patients undergoing cardiac surgical procedures with heart failure or low cardiac index, high-risk patients undergoing angioplasty, and high-risk patients undergoing coronary artery bypass grafting.

BACKGROUND

Prior art assistive heart devices such as the inter-aortic balloon pump (IABP) and the left ventricular assist device (LVAD) are indicated for cardiogenic shock conditions and inherently have a high risk of infection because of the surgical location and surgical complexity of installation. What is needed is a pre-cardiogenic minimally invasive heart assist device.

SUMMARY

A minimally invasive pre-cardiogenic heart assist device has been developed. A method of increasing myocardial blood flow using a Subclavian Diastolic Augmentation Device (SDAD) includes grafting a subclavian vein to a first synthetic chamber, the first synthetic chamber located inside of a body of the patient; grafting a subclavian artery to a second synthetic chamber, the second synthetic chamber located inside of the body of the patient; and pumping blood from the first synthetic chamber to the second synthetic chamber with a pump located inside of the body of the patient.

The SDAD may be indicated for conditions such as pre-cardiogenic shock, hemodynamic instability due to myocardial infarction, high-risk patients undergoing cardiac surgical procedures with heart failure or low cardiac index, high-risk patients undergoing angioplasty, and high-risk patients undergoing coronary artery bypass grafting.

The pump may be located in a third synthetic chamber positioned between the first synthetic chamber and the second synthetic chamber. The method may further comprise sensing a first blood pressure prior to entry into the first synthetic chamber. The method may further comprise sensing a second blood pressure within the first synthetic chamber. The method may further comprise sensing a third blood pressure within the second synthetic chamber. The method may further comprise sensing a fourth blood pressure after the second synthetic chamber. The method may further comprise detecting or predicting a dicrotic notch of a blood pressure waveform using the first blood pressure, the second blood pressure, the third blood pressure or the fourth blood pressure. The detecting or predicting of the dicrotic notch may trigger the pumping of blood from the first synthetic chamber to the second synthetic chamber. The pumping of blood may deliver between 50 ml to 5000 ml per minute from the first synthetic chamber to the second synthetic chamber. The volumes of the first synthetic chamber and the second synthetic chamber may be equal volumes between 5 ml and 50 ml.

An assistive heart device includes a first synthetic chamber, a second synthetic chamber, a third synthetic chamber connecting the first synthetic chamber to the second synthetic chamber, the third synthetic chamber housing a pump; a driver circuit for driving the pump, one or more pressure sensors; and using the driver circuit to trigger the pump based, at least partially, on a reading of the one or more pressure sensors.

A reading of one or more sensors may be used to detect or predict a dicrotic notch of a blood pressure waveform. The detecting or predicting of the dicrotic notch may trigger a pumping of blood from the first synthetic chamber to the second synthetic chamber. The pumping of blood may deliver between 50 ml to 5000 ml per minute from the first synthetic chamber to the second synthetic chamber. The volumes of the first synthetic chamber and the second synthetic chamber may be equal volumes between 5 ml and 50 ml. The pumping of blood may increase blood flow during diastole. The assistive heart device may further comprise an anti-coagulant injection line attached to the first synthetic chamber. The first synthetic chamber or the second synthetic chamber may further comprise an inner lining consisting of graphene, heparin, or a combination thereof. The first synthetic chamber or the second synthetic chamber may be impregnated with graphene, heparin, or a combination thereof. The pump may further comprise diamond or a diamond alloy.

A Subclavian Diastolic Augmentation Device (SDAD) and method for increasing myocardial blood flow has been developed. The SDAD module is indicated in the treatment of drug-resistant acute heart failure attributable to causes such as pre-cardiogenic shock as an important differentiating feature from other prior art devices that are indicated for cardiogenic shock.

In one embodiment, a SDAD of the present invention is installed when a catheter is inserted percutaneously/transvascularly without chest-opening surgery. Blood is aspirated via the tip of a catheter inserted/placed into the left ventricle and pumped out via the outlet port located in the ascending aorta, thereby assisting with antegrade blood circulation in the body. Improved hemodynamics and recovery of the heart muscles is achieved through prompt assistance of retrograde blood flow through the subclavian artery in a minimally invasive manner while reducing burden on the heart muscles, allowing for prompt recovery of cardiac function, by improving coronary artery flow during diastole only.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

It will be readily understood that the components of the present invention, as generally described and illustrated in the Figures herein, could be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings.

Figure 1:
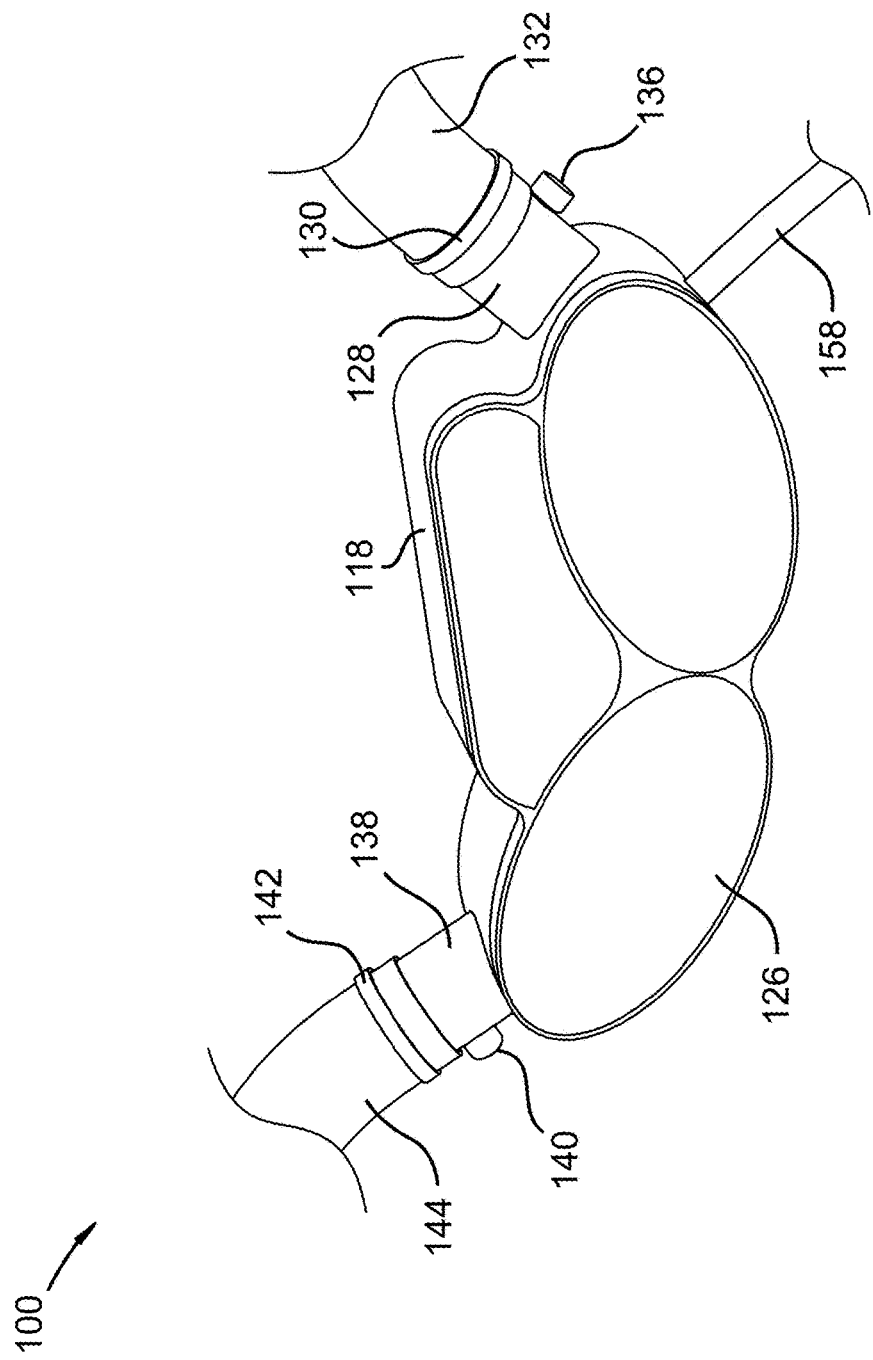
FIG. 1 shows a front view of a Subclavian Diastolic Augmentation Device in accordance with an embodiment of the invention.

FIG. 1 shows a Subclavian Diastolic Augmentation Device (SDAD) 100 including a main body portion 118, main body cover 126, anti-coagulation line 158, venous nozzle 128, arterial nozzle 138, first and second pressure sensors/transducers 136, third and fourth pressure sensors/transducers 140, graft veins 144/132, and retainer rings 130/142. Main body portion 118 includes a venous chamber, an arterial chamber, and a pump chamber. Main body portion may also house a controller, communication circuitry, pump and motor, motor control circuitry, one or more batteries, one or more microprocessors, memory, and programming allowing for functional operation of the SDAD. The venous, arterial chambers, and nozzles 138/128 may be constructed of or lined with heparin impregnated ePTFE and/or a graphene mixture. Graft veins 144/132 may be veins taken from a patient's leg or other body area. Graft veins 144/132 may include natural one-way valves allowing blood flow in one direction. In an alternate embodiment, Graft veins 144/132 may be artificial grafts with synthetic valves. Pressure sensors 136 may comprise two or more sensors with pressure sensing leads extending into vein 132 and into the venous chamber. Pressure sensors 140 may comprise two or more sensors with pressure sensing leads extending into vein 144 and into the arterial chamber. Retainer rings 130/142 are used to provide pressure to seal veins 132/144 against nozzles 128/138. Retainer rings 130/142 may be a crimped ring made of a medical grade metal alloy or may be a medical grade elastomeric material.

Figure 2:
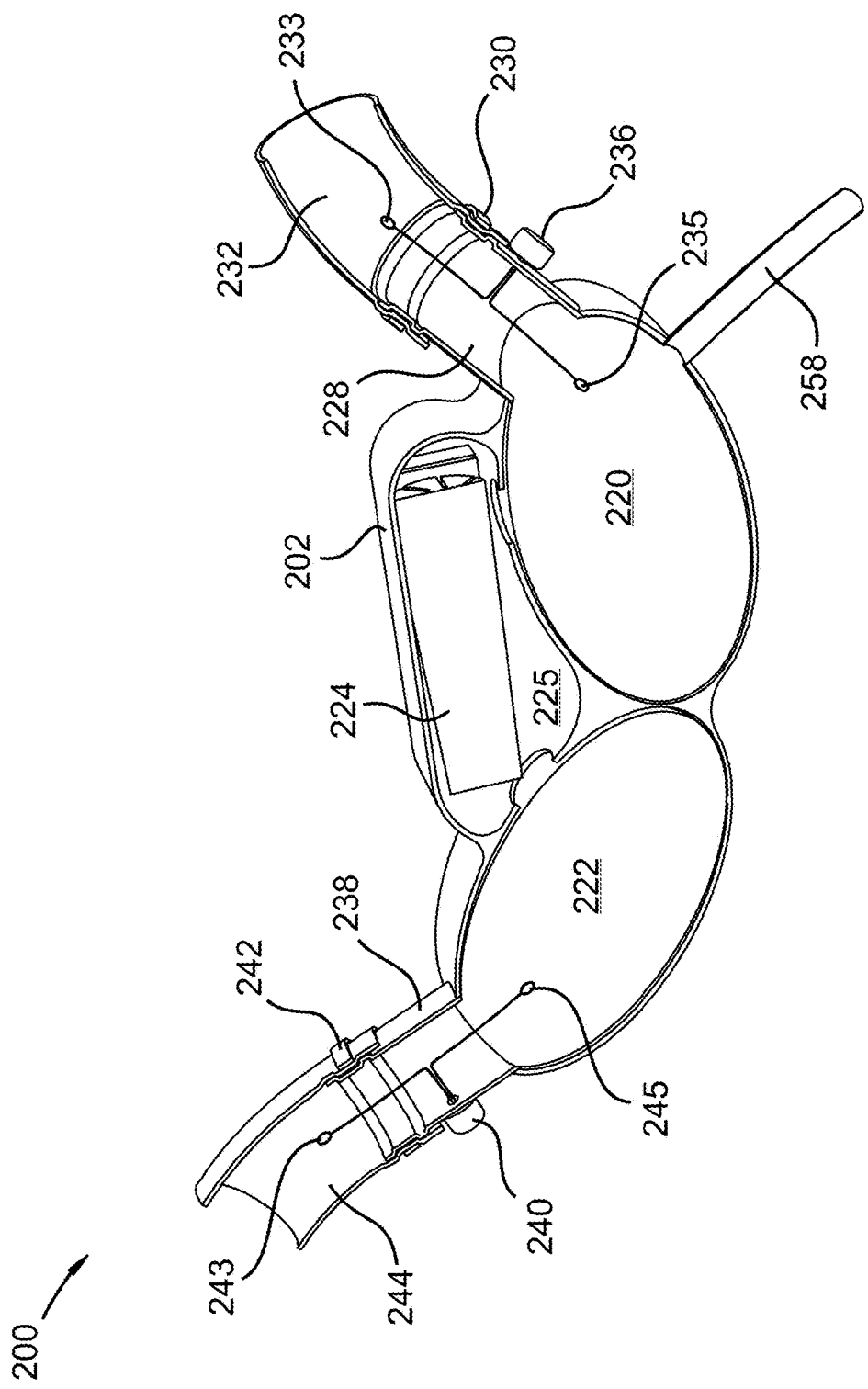
FIG. 2 shows a cross-sectional view of a Subclavian Diastolic Augmentation Device in accordance with an embodiment of the invention.

FIG. 2 shows a cross-sectional view 200 of a Subclavian Diastolic Augmentation Device (SDAD) including a main body portion 202, pump 224, anti-coagulation line 258, venous nozzle 228, arterial nozzle 238, venous chamber 220, arterial chamber 222, pump chamber 225, first and second pressure sensors/transducers 236, third and fourth pressure sensors/transducers 240, graft veins 244/232, and retainer rings 230/242. Main body portion 202 includes a venous chamber 220, an arterial chamber 222, and a pump chamber 225. Main body portion may also house a controller, communication circuitry, pump and motor, motor control circuitry, one or more batteries, one or more microprocessors, memory, and programming allowing for functional operation of the SDAD inside of chamber 225. The venous, arterial chambers 220/222, and nozzles 238/228 may be constructed of or lined with heparin impregnated ePTFE and/or a graphene mixture. Graft veins 244/232 may be veins taken from a patient's leg or other body area. Graft veins 244/232 may include natural one-way valves allowing blood flow in one direction. In an alternate embodiment, Graft veins 244/232 may be artificial grafts with synthetic valves. Pressure sensors 236 may comprise two or more sensors with pressure sensing leads 233/235 extending into vein 232 and into the venous chamber 220. Pressure sensors 240 may comprise two or more sensors with pressure sensing leads 243/245 extending into vein 244 and into the arterial chamber 222. Pressure sensing leads 233/235/243/245 may be ridged allowing the pressure sensing leads to stay in a proper location while blood is flowing. Retainer rings 230/242 are used to provide pressure to seal veins 232/244 against nozzles 228/238. Retainer rings 230/242 may be a crimped ring made of a medical grade metal alloy or may be a medical grade elastomeric material. Nozzles 228/238 may include one or more raised shoulder portions 241/231 allowing retainer rings 230/242 to seal against shoulder portions 241/231. Pump 224 may be an axial blood flow pump with a hydro dynamically suspended magnetic rotor, a centrifugal pump, or any other known medically suitable blood pump. Pump 224 may be initiated or triggered to speed up to a maximum setpoint during a dicrotic notch of a blood pressure waveform or during diastole and to slow down during systole. Pump 224 ejects a pulsed volume of blood from a subclavian vein into a subclavian artery with every heartbeat or with any multiple of a heartbeat. Minimum and maximum velocities, average velocities, pump motor timing, pump motor speeds, and pump volumes may be set, adjusted, and controlled with a controller located within housing 202. Timing algorithms based on dicrotic notch and prediction of dicrotic notch timings are known in the art and disclosed in a publication by Schreuder et. al. titled "Automatic Intraaortic Ballon Pump Timing Using an Intrabeat Dicrotic Notch Prediction Algorithm", 2005 which is hereby incorporated by reference, in its entirety, for all it teaches and discloses.

Figure 3:
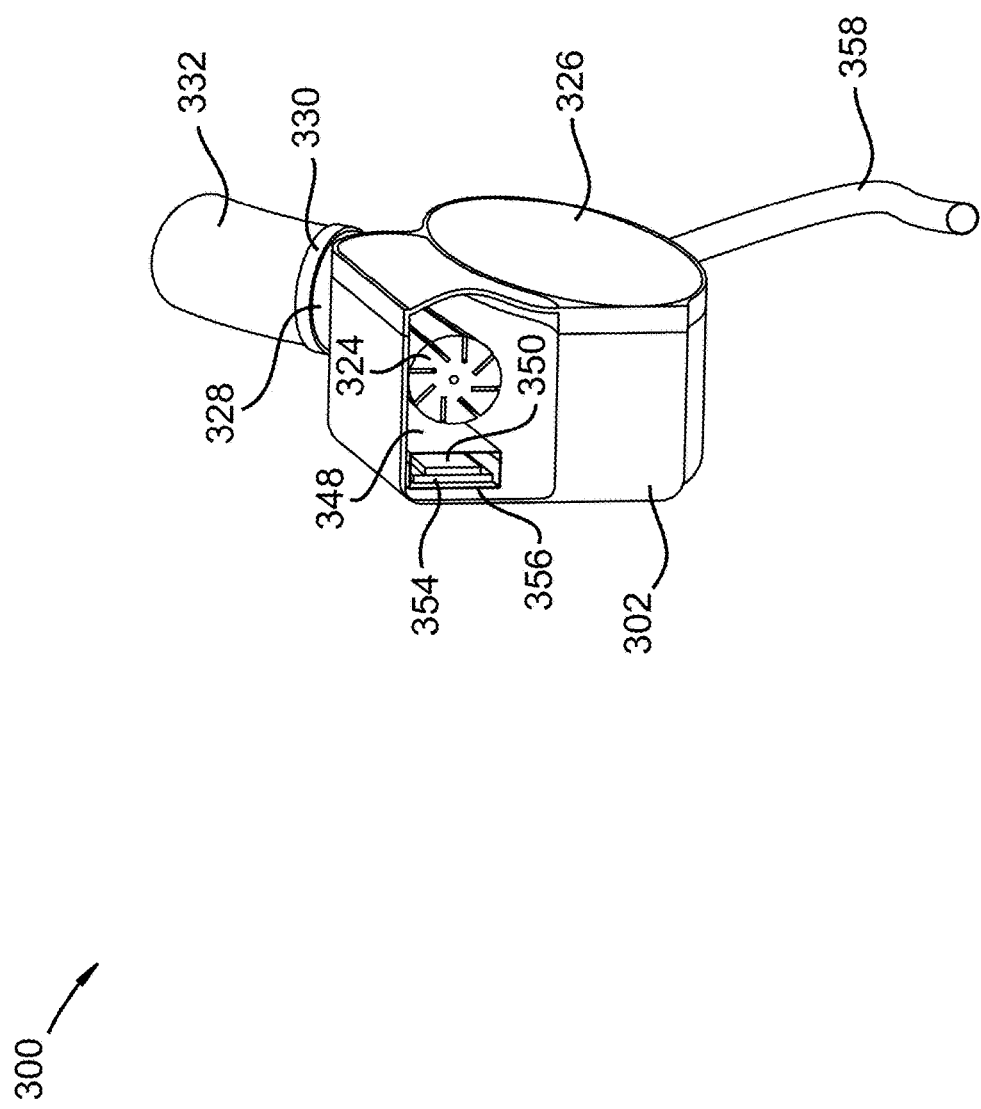
FIG. 3 shows a cross-sectional view of a Subclavian Diastolic Augmentation Device in accordance with an embodiment of the invention.

FIG. 3 shows a cross-sectional view 300 of a Subclavian Diastolic Augmentation Device (SDAD) including a main body portion 302, main body cover 326, anti-coagulation line 358, venous nozzle 328, graft vein 332, and retainer ring 330. Main body portion 302 includes a venous chamber, an arterial chamber, and a pump chamber. Main body portion may also house a controller 350, communication circuitry 350, pump and motor 324, motor control circuitry 350, one or more batteries 354, one or more microprocessors 350, memory 350, and programming within a fourth chamber 356 within third chamber 348. The venous, arterial chambers, and nozzles may be constructed of or lined with heparin impregnated ePTFE and/or a graphene mixture. Graft veins may be veins taken from a patient's leg or other body area. Graft veins may include natural one-way valves allowing blood flow in one direction. In an alternate embodiment, Graft veins may be artificial grafts with synthetic valves. Pressure sensors may comprise two or more sensors and connect to control circuitry 350. Pump 324 may be an axial blood flow pump with a hydro dynamically suspended magnetic rotor. Pump 324 may be initiated or triggered to speed up to a maximum setpoint during a dicrotic notch of a blood pressure waveform or during diastole and to slow down during systole. Pump 324 ejects a pulsed volume of blood from a subclavian vein into a subclavian artery with every heartbeat or with any multiple of a heartbeat. Minimum and maximum velocities, average velocities, pump motor timing, pump motor speeds, and pump volumes may be set, adjusted, and controlled with a controller located within housing 302. Timing algorithms based on dicrotic notch and prediction of dicrotic notch timings are known in the art and disclosed in a publication by Schreuder et. al. titled "Automatic Intraaortic Ballon Pump Timing Using an Intrabeat Dicrotic Notch Prediction Algorithm", 2005 which is hereby incorporated by reference, in its entirety, for all it teaches and discloses.

Figure 4:
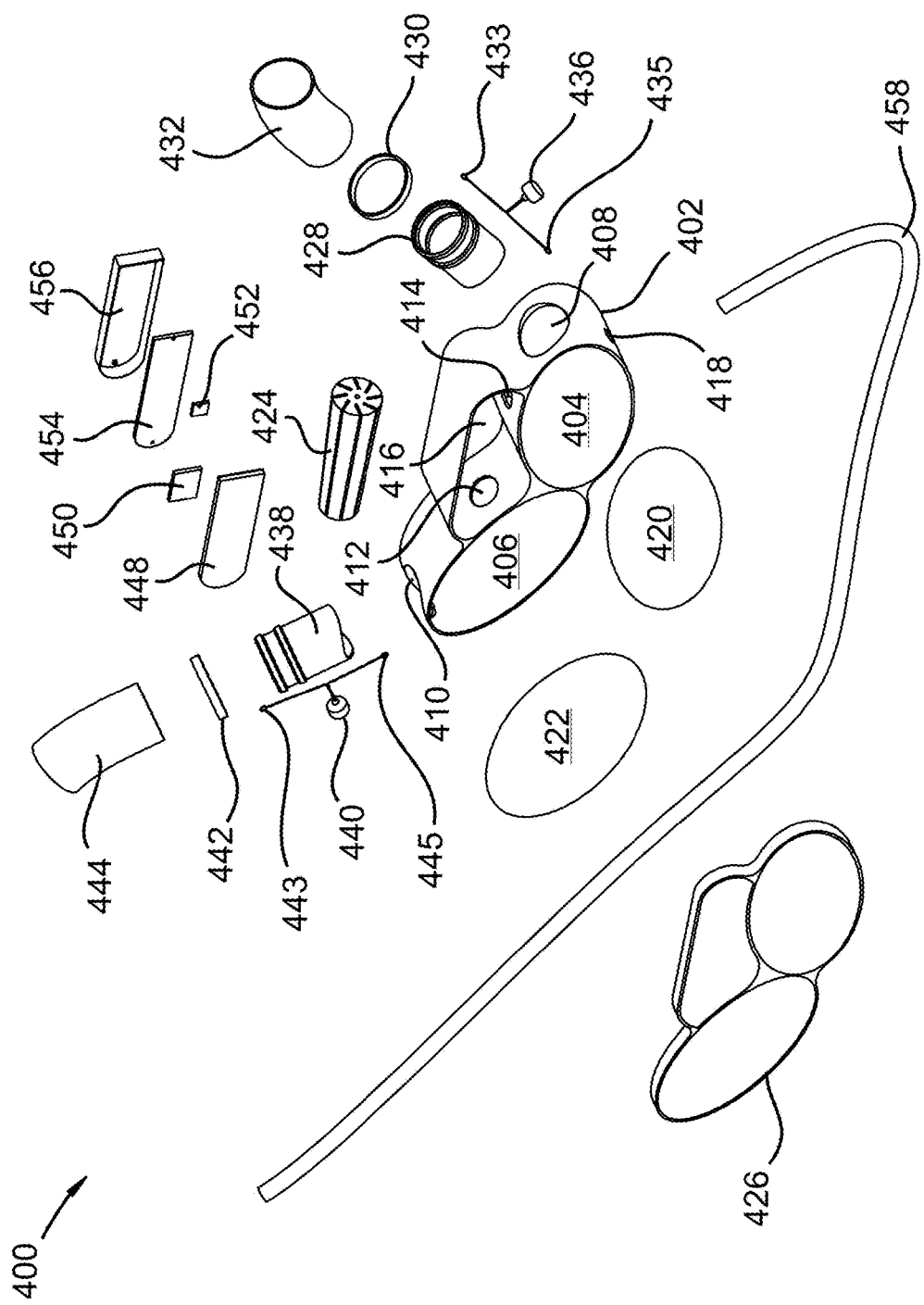
FIG. 4 shows an exploded view of a Subclavian Diastolic Augmentation Device in accordance with an embodiment of the invention.

FIG. 4 shows an exploded view 400 of a Subclavian Diastolic Augmentation Device (SDAD) including a main body portion 402, pump 424, anti-coagulation line 458, venous nozzle 428, arterial nozzle 438, venous chamber lining 420, arterial chamber lining 422, pump chamber 416, first and second pressure sensors/transducers 436, third and fourth pressure sensors/transducers 440, graft veins 444/432, and retainer rings 430/442. Main body portion 402 includes a venous chamber 404, an arterial chamber 406, and a pump chamber 416. Main body portion may also house a controller 450, communication circuitry 450, pump and motor 424, motor control circuitry 450, one or more batteries 452, one or more microprocessors 450, memory 450, and programming allowing for functional operation of the SDAD inside of chamber 456 and chamber cover 448. The venous, arterial chambers 420/422/404/406, and nozzles 438/428 may be constructed of or lined with heparin impregnated ePTFE and/or a graphene mixture. Graft veins 444/432 may be veins taken from a patient's leg or other body area. Graft veins 444/432 may include natural one-way valves allowing blood flow in one direction. In an alternate embodiment, Graft veins 444/432 may be artificial grafts with synthetic valves. Pressure sensors 436 may comprise two or more sensors with pressure sensing leads 433/435 extending into vein 432 and into the venous chamber 420/404. Pressure sensors 440 may comprise two or more sensors with pressure sensing leads 443/445 extending into vein 444 and into the arterial chamber 422/406. Pressure sensing leads 433/435/443/445 may be ridged allowing the pressure sensing leads to stay in a proper location while blood is flowing. Retainer rings 430/442 are used to provide pressure to seal veins 432/444 against nozzles 428/438. Retainer rings 430/442 may be a crimped ring made of a medical grade metal alloy or may be a medical grade elastomeric material. Nozzles 428/438 may include one or more raised shoulder portions 441/431 allowing retainer rings 430/442 to seal against shoulder portions 441/431. Pump 424 may be an axial blood flow pump with a hydro dynamically suspended magnetic rotor. Pump 424 may be initiated or triggered to speed up to a maximum setpoint during a dicrotic notch of a blood pressure waveform or during diastole and to slow down during systole. Pump 424 ejects a pulsed volume of blood from a subclavian vein into a subclavian artery with every heartbeat or with any multiple of a heartbeat. Minimum and maximum velocities, average velocities, pump motor timing, pump motor speeds, and pump volumes may be set, adjusted, and controlled with a controller located within housing 402. Timing algorithms based on dicrotic notch and prediction of dicrotic notch timings are known in the art and disclosed in a publication by Schreuder et. al. titled "Automatic Intraaortic Ballon Pump Timing Using an Intrabeat Dicrotic Notch Prediction Algorithm", 2005 which is hereby incorporated by reference, in its entirety, for all it teaches and discloses.

Figure 5:
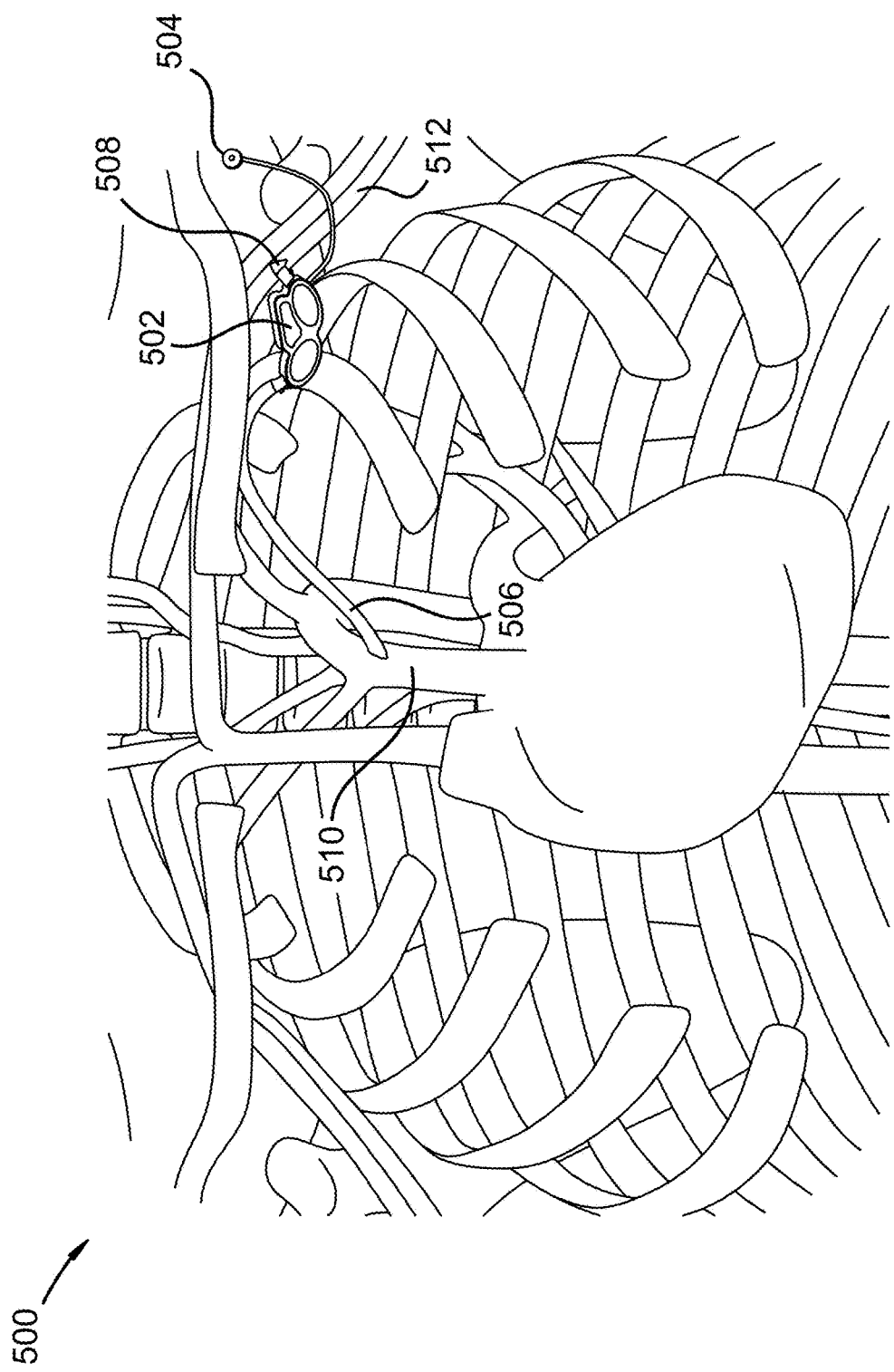
FIG. 5 shows an installed Subclavian Diastolic Augmentation Device in accordance with an embodiment of the invention.
Figure 6:
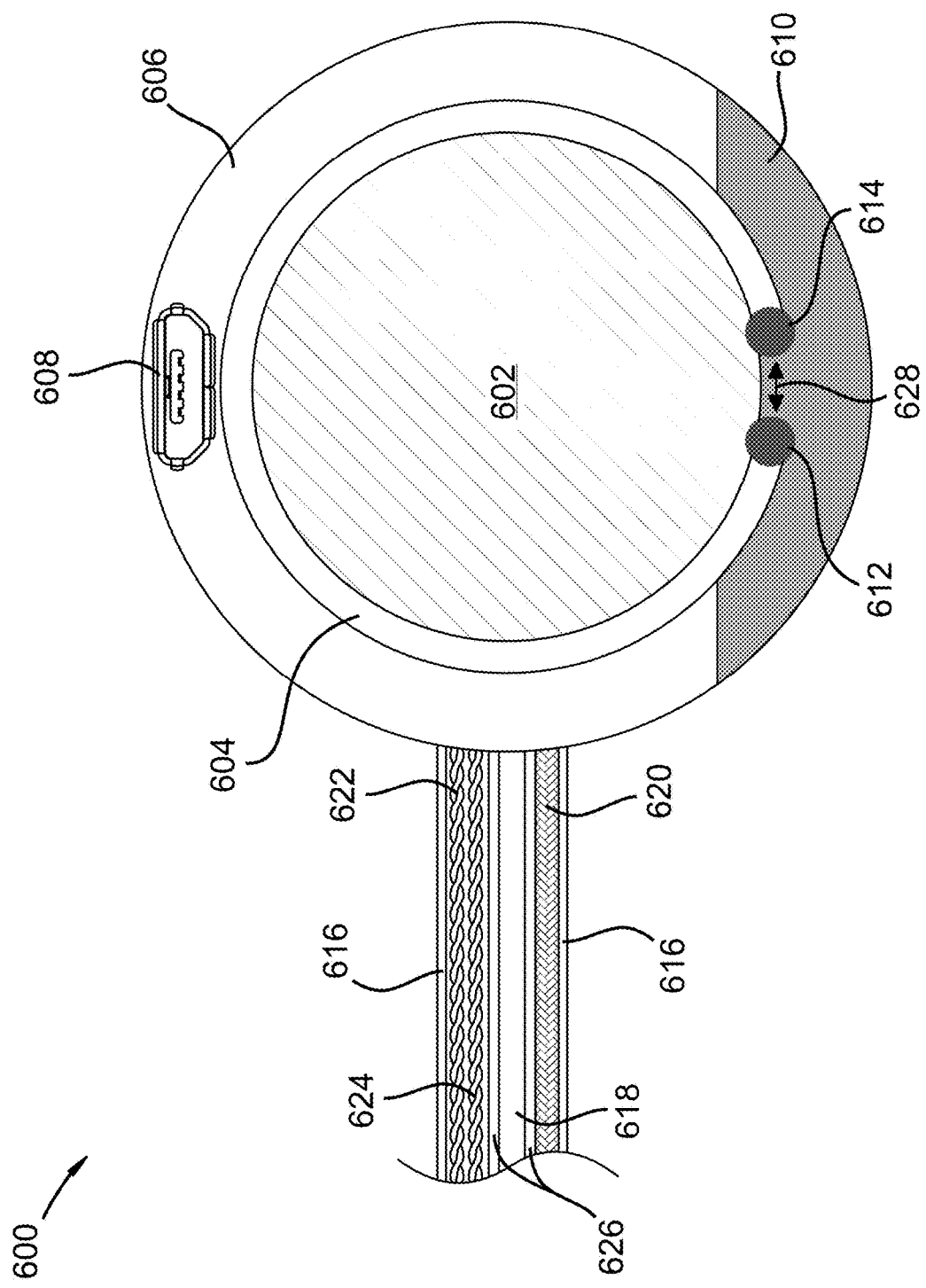
FIG. 6 shows a front view of an injection port in accordance with an embodiment of the invention.

FIG. 5 shows an installed Subclavian Diastolic Augmentation Device 502 in a patient 500 in accordance with an embodiment of the invention. SDAD 502 is grafted in between a subclavian vein 508 and a subclavian artery 510 using a vein graft 506. Anti-coagulant port 504 connects to a venous chamber of SDAD 502 and provides heparin or another anti-coagulant to SDAD 502. Port 504 may also include electrical power, data and wireless communications with SDAD as shown in FIG. 6. The placement of the SDAD is shown in one possible location but may be placed in other areas of the body such as close to the right shoulder, close to the left shoulder, between the heart and right shoulder, between the heart and left shoulder, and any other body area allowing grafts to a subclavian vein and a subclavian artery. A preferred placement area may include an area slightly closer to the shoulder than is shown in FIG. 5.

FIG. 6 shows a front view 600 of an injection port 602 in accordance with an embodiment of the invention. Injection Port 602 may include an antenna 604, an antenna element 610, antenna feed points 612/614, a feed point gap 628, a power/data port 608, a frame portion 606, a needle injection port 602, an anti-coagulant line/heparin line 618, power wire 622, data wires 624, antenna wires 620, and insulation material 616/626. A cover plate (not shown) may plug into port 608 and completely cover injection port 602/606. Antenna 604 may be a broadband ring antenna, a balun type antenna, a MIMO antenna, a microstrip antenna, a printed microstrip antenna, or any other small feature size antenna. Antenna 604 may simultaneously operate in multiple bandwidths such as Bluetooth, WIFI, GSM, and/or CMDA. Antenna element 610 may be a directional antenna element, a parasitic antenna element, or a front focusing antenna element. It may be desirable to focus electromagnetic waves in a forward direction canceling out rear lobe transmission into a patient. Antenna element 610 may work as a ground plane for antenna 604 and work to minimize or cancel rear lobe transmission while focusing energy in a forward direction. Antenna feed line 620 may be a coaxial feed line or may contain two or more phased array signals from a phased array transmission system within the SDAD. Power/Data port 608 may be used to charge batteries in the SDAD, to directly power the SDAD, to communicate/program the SDAD, and to perform maintenance functions on the SDAD. Antenna feed point gap 628 may be used to optimize impedance, band, and transmit power of antenna 604.

Figure 7:
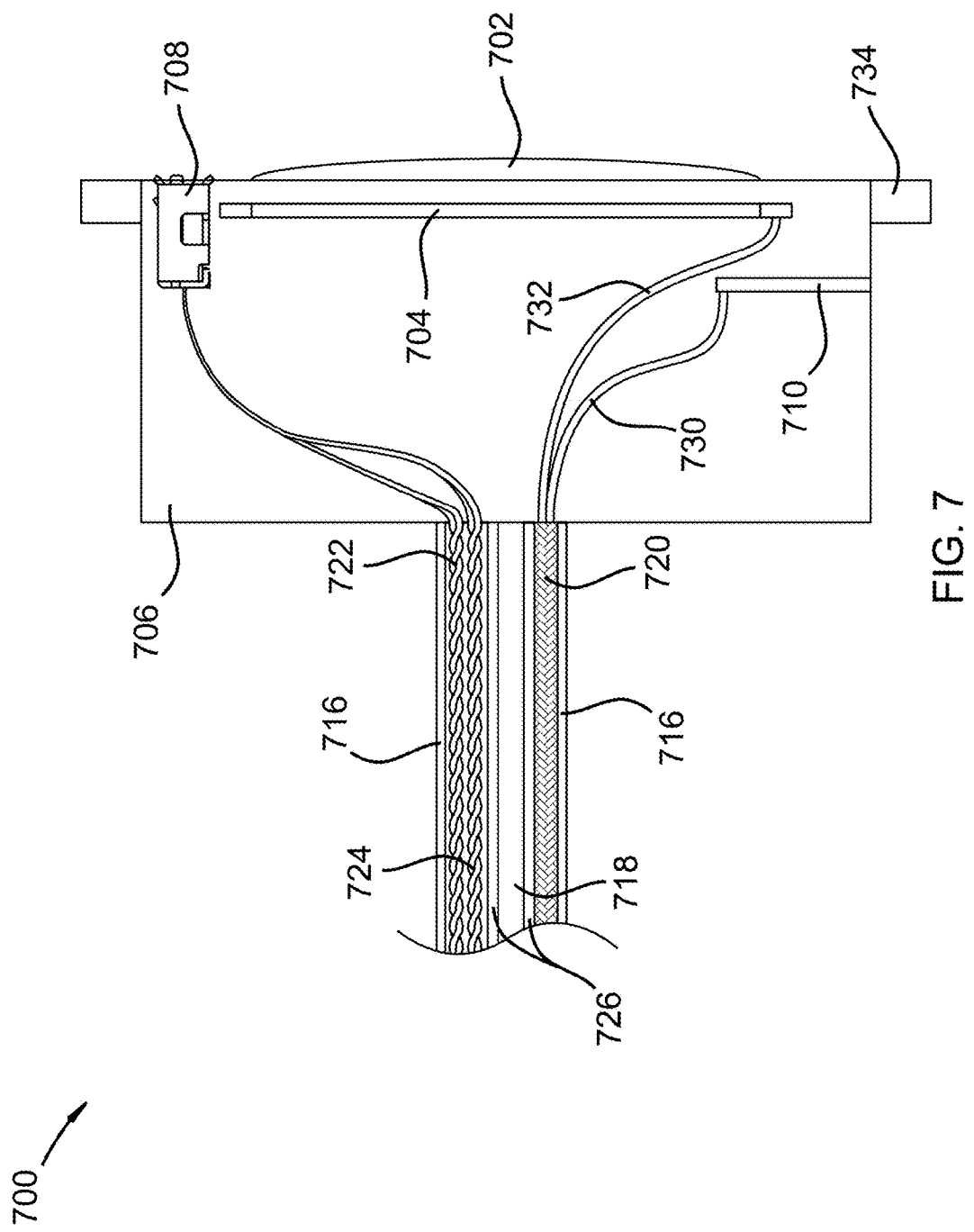
FIG. 7 shows a side view of an injection port in accordance with an embodiment of the invention.

FIG. 7 shows a side view 700 of an injection port 702 in accordance with an embodiment of the invention. Injection Port 702 may include an antenna 704, an antenna element 710, antenna feed lines 732/730, a power/data port 708, a frame portion 734, a needle injection port 702, an anti-coagulant line/heparin line 718, power wire 722, data wires 724, antenna wires 720, and insulation material 716/726. A cover plate (not shown) may plug into port 708 and completely cover injection port 702/706. Antenna 704 may be a broadband ring antenna, a balun type antenna, a MIMO antenna, a microstrip antenna, a printed microstrip antenna, or any other small feature size antenna. Antenna 704 may simultaneously operate in multiple bandwidths such as Bluetooth, Wifi, GSM, and/or CMDA. Antenna element 710 may be a directional antenna element, a parasitic antenna element, or a front focusing antenna element. It may be desirable to focus electromagnetic waves in a forward direction canceling out rear lobe transmission into a patient. Antenna element 710 may work as a ground plane for antenna 704 and work to minimize or cancel rear lobe transmission while focusing energy in a forward direction. Antenna feed line 720 may be a coaxial feed line or may contain two or more phased array signals from a phased array transmission system within the SDAD. Power/Data port 708 may be used to charge batteries in the SDAD, to directly power the SDAD, to communicate/program the SDAD, and to perform maintenance functions on the SDAD. Body portion 706 may include an anti-coagulation pressure vessel (not shown) and metering device for metering anti-coagulants to the SDAD over time.

Figure 8:
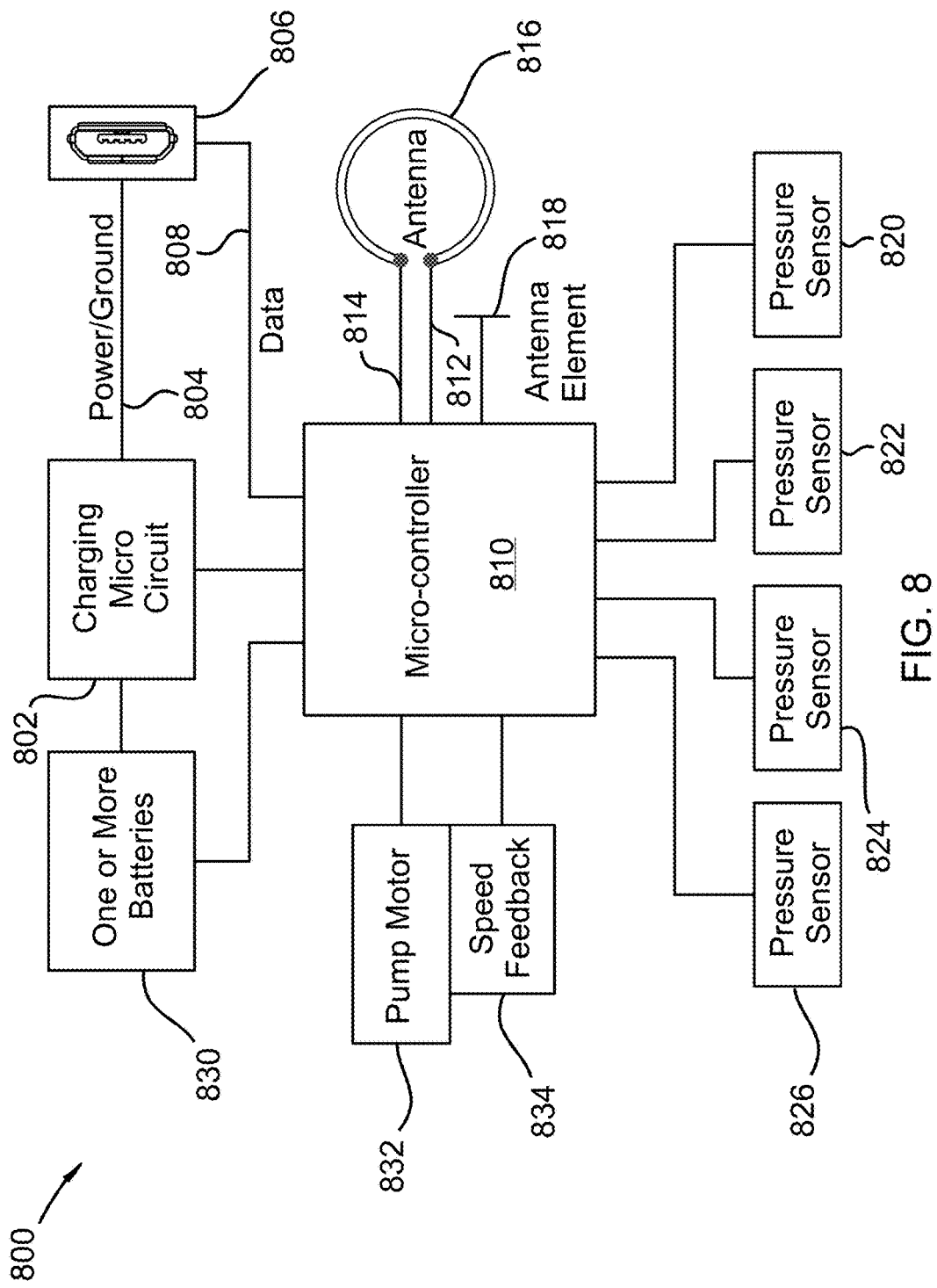
FIG. 8 shows a schematic diagram of a Subclavian Diastolic Augmentation Device in accordance with an embodiment of the invention.

FIG. 8 shows a schematic diagram 800 of a Subclavian Diastolic Augmentation Device in accordance with an embodiment of the invention. Micro-controller 810 may contain one or more microprocessors with memory and programming to control pump motor functions, control settings, user interface software, maintenance software settings, battery charging functions, wireless communication protocols, pressure sensor sampling routines, input and output functions, and needed operational software. Pump Motor 832 may be controlled by an embedded motor controller within controller 810. Motor control settings may include settings such as acceleration/deceleration, speeds, ramp up, ramp down, idle speed controls, max speed, min speed, and energy saving functions upon detection of a low battery. Pump 224 may be an axial blood flow pump with a hydro dynamically suspended magnetic rotor. Pump 224 may be initiated or triggered to speed up to a maximum setpoint during a dicrotic notch of an arterial wave form or during diastole and to slow down during systole. Pump 832 ejects a pulsed volume of blood from a subclavian vein into a subclavian artery with every heartbeat or with any multiple of a heartbeat. Minimum and maximum velocities, average velocities, pump motor timing, pump motor speeds, and pump volumes may be set, adjusted, and controlled with controller 810. Speed feedback 834 may be an encoder within pump motor 832 or may be a result of magnetic pules or back emf signals. Pressure sensors 826-820 are medical grade pressure transducers providing a changing capacitance, inductance, reactance, resistance or a combination thereof. One or more batteries 830 are internal batteries but external batteries may be plugged in to port 806 and provide auxiliary power to the SDAD and/or charge one or more batteries 830. Micro charging circuit 802 is used to optimize charging and discharging of one or more batteries 803. In one example, Micro charging circuit is embedded within micro-controller 810 and functions to charge one or more batteries 830 between 50% and 80% of full capacity. Antenna element 818 may be used to direct or block back lobe antenna radiation from entering a patient using a SDAD. Antenna 816 may be a loop antenna, a phased array antenna, or a MIMO antenna. Micro-controller may provide transmit and receive signals allowing antenna 816 to wireless communicate with smartphones, computers, and other devices.

Figure 9:
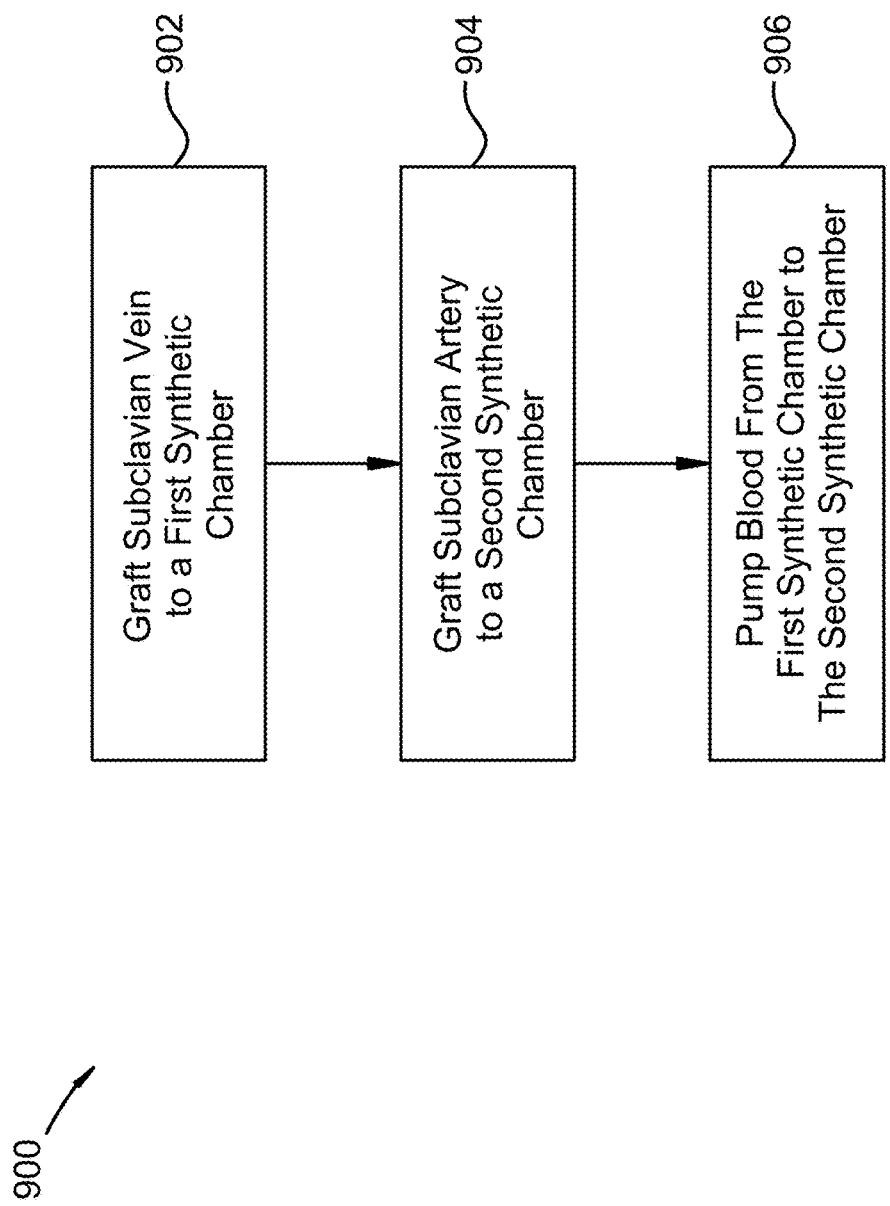
FIG. 9 shows a method flow chart of a Subclavian Diastolic Augmentation Device in accordance with an embodiment of the invention.

FIG. 9 shows a method flow chart 900 of a Subclavian Diastolic Augmentation Device in accordance with an embodiment of the invention. A minimally invasive pre-cardiogenic heart assist device has been developed. A method of increasing myocardial blood flow using a Subclavian Diastolic Augmentation Device (SDAD) includes grafting a subclavian vein to a first synthetic chamber 902, the first synthetic chamber located inside of a body of the patient; grafting a subclavian artery to a second synthetic chamber 904, the second synthetic chamber located inside of the body of the patient; and pumping blood from the first synthetic chamber to the second synthetic chamber 906 with a pump located inside of the body of the patient.

Figure 10:
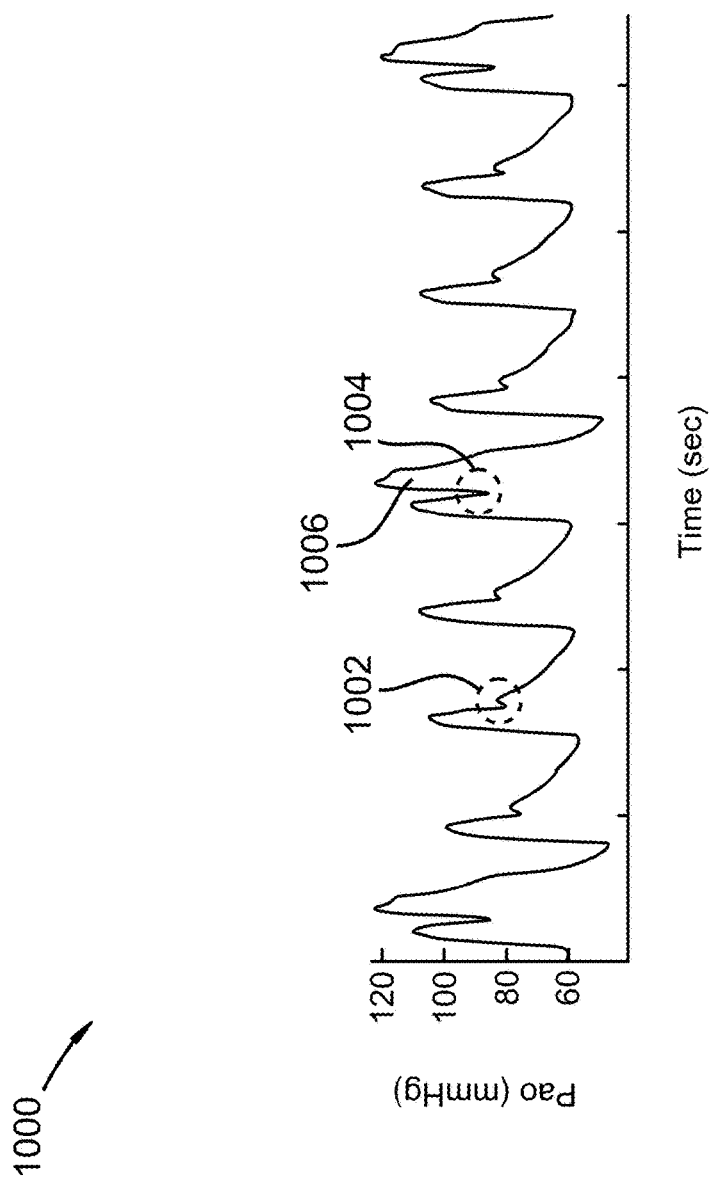
FIG. 10 shows arterial blood pressures in accordance with an embodiment of the invention.

FIG. 10 shows arterial blood pressures 1000 in accordance with an embodiment of the invention. Here a one in four assist methodology has been implemented using an SDAD of the present invention. At 1002 a dicrotic notch of a blood pressure waveform is detected and pressures recorded within a memory of the SDAD. At 1004, the SDAD system has learned and recognized the notch and ramps up its pump motor increasing blood pressure and flow to a heart muscle during diastole 1006 and slows down the pump motor during systole. The SDAD waits for a fourth heart beat and provides another injection of blood into the heart. Other assist methodologies such as one to one, one to two, one to three may be used depending on blood delivery needs of specific applications/treatments.

The systems and methods disclosed herein may be embodied in other specific forms without departing from their spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of increasing myocardial blood flow in a patient comprising:
grafting a subclavian vein to a first synthetic chamber with a first liquid volume between 5 ml and 50 ml, the first synthetic chamber located inside of a body of the patient;
grafting a subclavian artery to a second synthetic chamber with a second liquid volume equal to the first liquid volume of the first synthetic chamber, the second synthetic chamber located inside of the body of the patient; and
pumping blood from the first synthetic chamber to the second synthetic chamber and from the second synthetic chamber towards an aortic valve using a pump located inside of the body of the patient during diastole.

2. The method of claim 1, wherein the pump is located in a third synthetic chamber positioned between the first synthetic chamber and the second synthetic chamber.

3. The method of claim 1, further comprising sensing a first blood pressure prior to entry into the first synthetic chamber.

4. The method of claim 3, further comprising sensing a second blood pressure within the first synthetic chamber.

5. The method of claim 4, further comprising sensing a third blood pressure within the second synthetic chamber.

6. The method of claim 5, further comprising sensing a fourth blood pressure after the second synthetic chamber.

7. The method of claim 6, further comprising detecting or predicting a dicrotic notch of a blood pressure wave form using the first blood pressure, the second blood pressure, the third blood pressure or the fourth blood pressure.

8. The method of claim 7, wherein the detecting or predicting of the dicrotic notch triggers the pumping of blood from the first synthetic chamber to the second synthetic chamber.

9. The method of claim 1, wherein the pumping of blood delivers between 50 ml to 5000 ml per minute from the first synthetic chamber to the second synthetic chamber.

10. An assistive heart device comprising:
a first synthetic chamber, with a first liquid volume between 5 ml and 50 ml;
a second synthetic chamber, with a second liquid volume equal to the first liquid volume of the first synthetic chamber;

a third synthetic chamber connecting the first synthetic chamber to the second synthetic chamber, the third synthetic chamber housing a pump;

a driver circuit for driving the pump;

one or more pressure sensors; and wherein the driver circuit triggers the pump to eject blood into a subclavain artery from the second synthetic chamber towards an aortic valve during diastole based, at least partially, on a reading of the one or more pressure sensors.

11. The assistive heart device of claim 10, wherein the reading is used to detect or predict a dicrotic notch of a blood pressure waveform.

12. The assistive heart device of claim 11, wherein the detecting or predicting of the dicrotic notch triggers a pumping of blood from the first synthetic chamber to the second synthetic chamber.

13. The assistive heart device of claim 12, wherein the pumping of blood delivers between 50 ml to 5000 ml per minute from the first synthetic chamber to the second synthetic chamber.

14. The assistive heart device of claim 10, further comprising an anti-coagulant injection line attached to the first synthetic chamber.

15. The assistive heart device of claim 10, wherein the first synthetic chamber or the second synthetic chamber further comprise an inner lining consisting of graphene, heparin, or a combination thereof.

16. The assistive heart device of claim 10, wherein the first synthetic chamber or the second synthetic chamber are impregnated with graphene, heparin, or a combination thereof.

17. The assistive heart device of claim 10, wherein the pump further comprises diamond or a diamond alloy.

* * * * *